(12) United States Patent
Olivier

(10) Patent No.: US 8,353,538 B2
(45) Date of Patent: *Jan. 15, 2013

(54) CONNECTION DEVICES AND MALE-FEMALE CONNECTION SYSTEM COMPRISING THEM

(75) Inventor: Stephane Olivier, Rosheim (FR)

(73) Assignee: EMD Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/231,257

(22) Filed: Sep. 13, 2011

(65) Prior Publication Data

US 2012/0001424 A1    Jan. 5, 2012

Related U.S. Application Data

(62) Division of application No. 12/459,633, filed on Jul. 6, 2009, now Pat. No. 8,152,203.

(30) Foreign Application Priority Data

Jul. 23, 2008    (FR) ..................................... 08 55020

(51) Int. Cl.
*F16L 25/00* (2006.01)
(52) U.S. Cl. ............ 285/68; 285/67; 285/325; 604/905
(58) Field of Classification Search .................. 285/67, 285/68, 325; 604/199, 905
See application file for complete search history.

(56) References Cited

U.S. PATENT DOCUMENTS

| | | | |
|---|---|---|---|
| 3,690,344 A | 9/1972 | Brumm | |
| 4,431,424 A | 2/1984 | Svensson | |
| 6,039,302 A | 3/2000 | Cote, Sr. et al. | |
| 6,991,215 B2 | 1/2006 | Kiehne | |
| 2010/0021230 A1 | 1/2010 | Olivier | |
| 2012/0001423 A1 | 1/2012 | Olivier | |

FOREIGN PATENT DOCUMENTS

| | | |
|---|---|---|
| EP | 0226564 A1 | 6/1987 |
| EP | 1297861 A1 | 4/2003 |
| EP | 1747796 A1 | 1/2007 |
| FR | 2126704 A | 10/1972 |
| WO | 82/00698 A1 | 3/1982 |

OTHER PUBLICATIONS

French Search Report dated Mar. 2, 2009 in corresponding foreign patent application No. FR 0855020, 2 pages.
Office Action (Restriction) dated Jun. 13, 2011 in corresponding U.S. Appl. No. 12/459,633.
Office Action dated Sep. 13, 2011 in corresponding U.S. Appl. No. 12/459,633.
Notice of Allowance mailed Jan. 27, 2012 in corresponding U.S. Appl. No. 12/459,633.
Supplemental Notice of Allowance mailed Mar. 5, 2012 in corresponding U.S. Appl. No. 12/459,633.
Office Action mailed Jul. 3, 2012 in corresponding U.S. Appl. No. 13/231,247.
Notice of Allowance mailed Oct. 17, 2012 in corresponding U.S. Appl. No. 13/231,247.

*Primary Examiner* — David E Bochna
(74) *Attorney, Agent, or Firm* — Nields, Lemack & Frame, LLC

(57) ABSTRACT

A male-female connection device, wherein the male connection device includes a sleeve and a slide that is adapted to occupy, relative to the sleeve, a position in which the slide is advanced in the sleeve, the device also including a tubular film folded back on itself and pressed between the slide and the sleeve. The female connection device includes a sleeve and a slide that is adapted to occupy, relative to the sleeve, a position in which the slide is set back in the sleeve, the device also including a tubular film folded back on itself and pressed between the slide and the sleeve. The male and female connection devices can be engaged within each other.

16 Claims, 13 Drawing Sheets

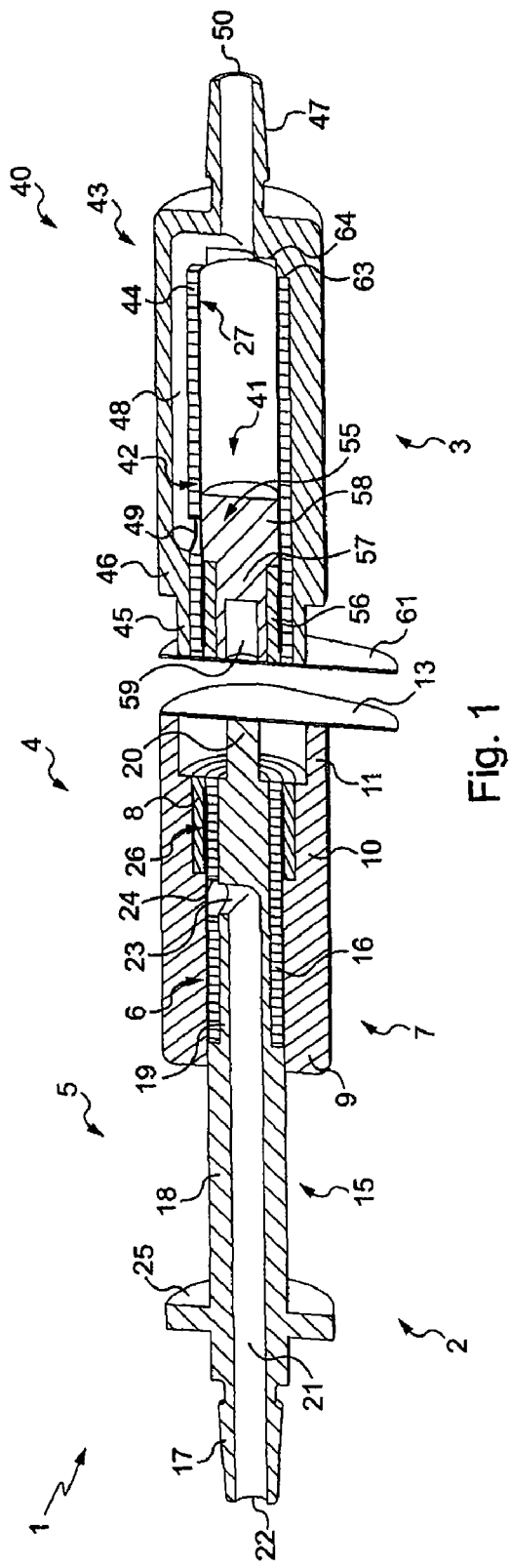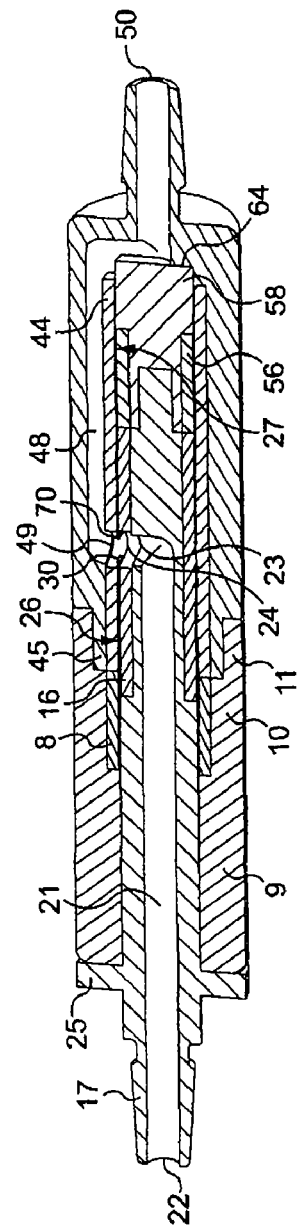
Fig. 1
Fig. 2

CONNECTION DEVICES AND MALE-FEMALE CONNECTION SYSTEM COMPRISING THEM

This application is a divisional of U.S. patent application Ser. No. 12/459,633, filed Jul. 6, 2009, now U.S. Pat. No. 8,152,203, which claims priority of French Patent Application No. 0855020 filed on Jul. 23, 2008, the disclosures of which are incorporated herein by reference.

FIELD

The present invention concerns male-female connection systems.

In different fields of application, and in particular in the microbiological field (for the flow of fluids for example), it is particularly important to be able to make connections while ensuring that the surfaces that are to be placed in register with each other to form those connections remain fully isolated from the exterior environment, in particular in order to maintain their clean or even sterile character or else to protect those surfaces from germs, dust, gas and/or liquid in the vicinity.

BACKGROUND

Male-female connection systems already exist, as described in particular by the European patent EP 1 297 861, provided in particular for the microbiological field and for which the portions of surfaces of the male and female devices to connect are protected by a peelable film. On connecting these devices, the outer faces of these protective films are placed in contact with each other such that the contaminants/dust present on those faces are trapped between those films that are pressed against each other. The films are then simultaneously peeled in order to take with them the contaminants so encapsulated and to enable the male device to be engaged in the female device in order for the portions of surface to be connected.

SUMMARY

The invention aims to provide male and female devices of the same type but which are at the same time more sure and more practical.

To that end it provides a connection device for a male-female connection system characterized in that it comprises a male part provided with a sleeve and with a slide disposed within said sleeve, said device having a front face adapted to cooperate with a member to connect, said slide being adapted to occupy, relative to said sleeve, a starting position and a final position in which said slide is advanced in said sleeve relative to said starting position, said device also comprising a tubular film folded back on itself and pressed between the slide and the sleeve, the film having, on respective opposite sides of its fold, an inner portion in at least partially non-sliding contact with said slide and an outer portion in at least partially non-sliding contact with said sleeve whereas the inner and outer portions of the film, on movement of the slide in said sleeve from the starting position to the final position, are adapted to slide over each other by virtue of which said fold passes, on movement of said slide in said sleeve, from a position in which a portion of outer lateral surface of said slide is covered by said film to a position in which said portion of outer lateral surface is uncovered.

This device is thus provided to cooperate with a device provided with a female part in order to connect the portions of surfaces of those devices.

So long as no connection with a device provided with a complementary female part has been made, the surface portion present on the slide to be kept isolated from the exterior environment is covered by the tubular film pressed between the sleeve and the slide in order for that surface to be protected thereby.

When the connection with a device provided with a complementary female part occurs, because the film cooperates by a non-sliding contact with the sleeve and the slide, the relative movement of the slide relative to the sleeve drives the movement of the fold of the film relative to that surface portion such that the contaminants initially present on the front surface of the device are driven rearwards while being isolated from the surface portion to be connected by the film which rolls out.

The contaminants are thus encapsulated and moved away from the surface to connect, the movement of the fold relative to the slide also making it possible to uncover the portion of surface to connect to make it accessible to a similar portion of surface present on the device with a complementary female part.

Contrary to the devices of the prior art in which, after putting the male and female devices in contact, at least two operations are still necessary to place the clean surfaces in register with each other, i.e. peel the protective films and engage the male device in the female device, these two operations are carried out here in a single move by mere movement of the slide of the male device in the sleeve of that device from its starting position to its final position, such that the connection is made more practical here and without risk for example of having the operator forget to peel the protective films.

Furthermore, the tubular form of the film, leading to continuous and even compression of the film between the slide and the sleeve (without creation of any line of weakness in which air/water could penetrate), ensures perfect fluid-tightness for the zone to protect, so making it possible to perform such connections in all types of exterior environments (in a liquid milieu, for example).

This is also an advantage relative to the devices of the prior art provided with peelable films of flat form on the edge of which spaces could form locally which constitute accommodation for particles which are all potential sources of contamination, in particular when those edges pass in the neighborhood of the surface to protect when the film is peeled.

The device according to the invention thus ensures a sterile connection and not uniquely an aseptic one, this being independent of the exterior environment in which it is situated.

The invention also concerns a connection device for a male-female connection system characterized in that it comprises a female part provided with a sleeve and with a slide disposed within said sleeve, said device having a front face adapted to cooperate with a member to connect, said slide being adapted to occupy, relative to said sleeve, a starting position and a final position in which said slide is set back in said sleeve relative to said starting position, said device also comprising a tubular film folded back on itself and pressed between the slide and the sleeve, the film having, on respective opposite sides of its fold, an inner portion in at least partially non-sliding contact with said slide and an outer portion in at least partially non-sliding contact with said sleeve whereas the inner and outer portions of the film, on movement of the slide in said sleeve from the starting position to the final position, are adapted to slide over each other by virtue of which said fold passes, on movement of said slide in said sleeve, from a position in which a portion of inner lateral surface of said sleeve is covered by said film to a position in which said portion of inner lateral surface is uncovered.

In similar manner to the male part connection device, the female part connection device has the same advantages.

So long as no connection with a device provided with the complementary male part has been made, the surface portion present on the sleeve to be kept isolated from the exterior environment is covered by the tubular film pressed between the sleeve and the slide in order for that surface to be protected thereby.

When the connection with a device provided with a male part occurs, as the film cooperates by a non-sliding contact with the sleeve and the slide, the relative movement of the slide relative to the sleeve drives the movement of the fold of the film relative to that surface portion such that the contaminants initially present on the front surface of the device are isolated from the surface portion to be connected by the film which rolls in.

The contaminants are thus encapsulated and moved away from the surface to connect, the movement of the fold relative to the slide also making it possible to uncover the surface to connect to make it accessible to the similar surface present on the male part device.

According to features preferred for reasons of simplicity and convenience with regard both to manufacture and to use:
- said sleeve comprises a portion in a material adapted to ensure the non-sliding contact by friction against the outer portion of said film;
- said portion of said sleeve is of silicone;
- said slide comprises a portion in a material adapted to ensure the non-sliding contact by friction against the inner portion of said film;
- said portion of said slide is of silicone;
- said film is of polyurethane;
- in the starting position, said fold is withdrawn from said front face;
- in said starting position the front face of said device is obturated by a peelable film;
- said portion of outer lateral surface of the male part device comprises an opening for access to a duct formed in said slide;
- the male part device also comprises a female part provided with another sleeve and another slide disposed within said other sleeve, said device having another front face adapted to cooperate with a member to connect, said other slide being adapted to occupy, relative to said other sleeve, a starting position and a final position in which said slide is set back in said sleeve relative to said starting position, said device also comprising another tubular film folded back on itself and pressed between the slide and the sleeve, the film having on respective opposite sides of its fold an inner portion in at least partially non-sliding contact with said sleeve whereas the inner and outer portions of the film, on movement of the slide in said sleeve from the starting position to the final position, are adapted to slide over each other by virtue of which said fold passes, on movement of said slide in said sleeve, from a position in which a portion of inner lateral surface of said sleeve is covered by said film to a position in which said portion of inner lateral surface is uncovered; and/or
- said portion of inner lateral surface of the female part device comprises an opening for access to a duct formed in said sleeve.

The invention also concerns a male-female connection system characterized in that it comprises a male part connection device as set out above and a female part connection device as set out above, the male and female connection devices being provided to be engaged within each other, with the front faces of the devices being adapted to come into contact with each other, said slides being adapted to move in said sleeves to pass from their starting positions to their final positions, with, in their final positions, the portion of outer lateral surface of the slide of the male part device facing the portion of inner lateral surface of the sleeve of the female part device.

According to features preferred for reasons of simplicity and convenience with regard both to manufacture and to use:
- the male part device comprises snap-fastening means adapted to cooperate with complementary snap-fastening means that the female part device comprises to hold said devices fastened to each other; and/or
- the sleeve of the male part device comprises snap-fastening means adapted to cooperate with complementary snap-fastening means that the slide of that device comprises to hold the slide in its final position.

BRIEF DESCRIPTION OF THE DRAWINGS

The features and advantages of the invention will appear from the following description, given by way of preferred but non-limiting example, with reference to the accompanying drawings in which:

FIG. 1 is a perspective section view of male and female connection devices according to the invention in which a sleeve and a slide of the male connection device are on the point of being engaged in a sleeve and a slide of the female connection device;

FIG. 2 is a similar view to FIG. 1 but in which those sleeves and slides are represented in their engaged positions in which a duct of the slide of the male device is placed in communication with a duct of the sleeve of the female device.

DETAILED DESCRIPTION

Figure 3:
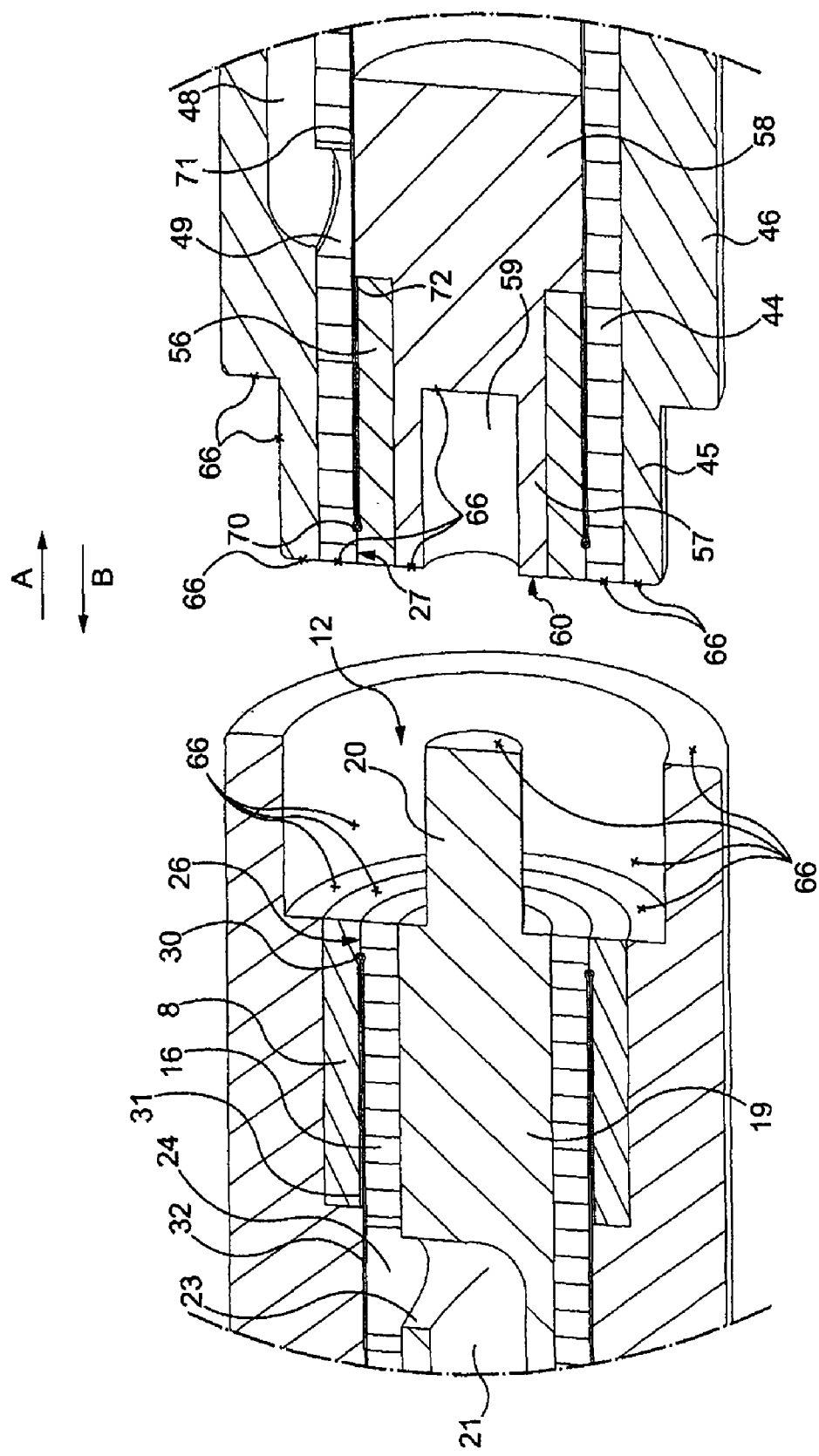
FIGS. 3 to 8 are six enlarged section views in perspective illustrating the different steps of movement of the slides of the devices relative to the sleeves, from a starting position of those slides in their sleeves, in which the duct of each device is obturated, to attain a final position of those slides in which those ducts are placed in communication with each other.
Figure 4:
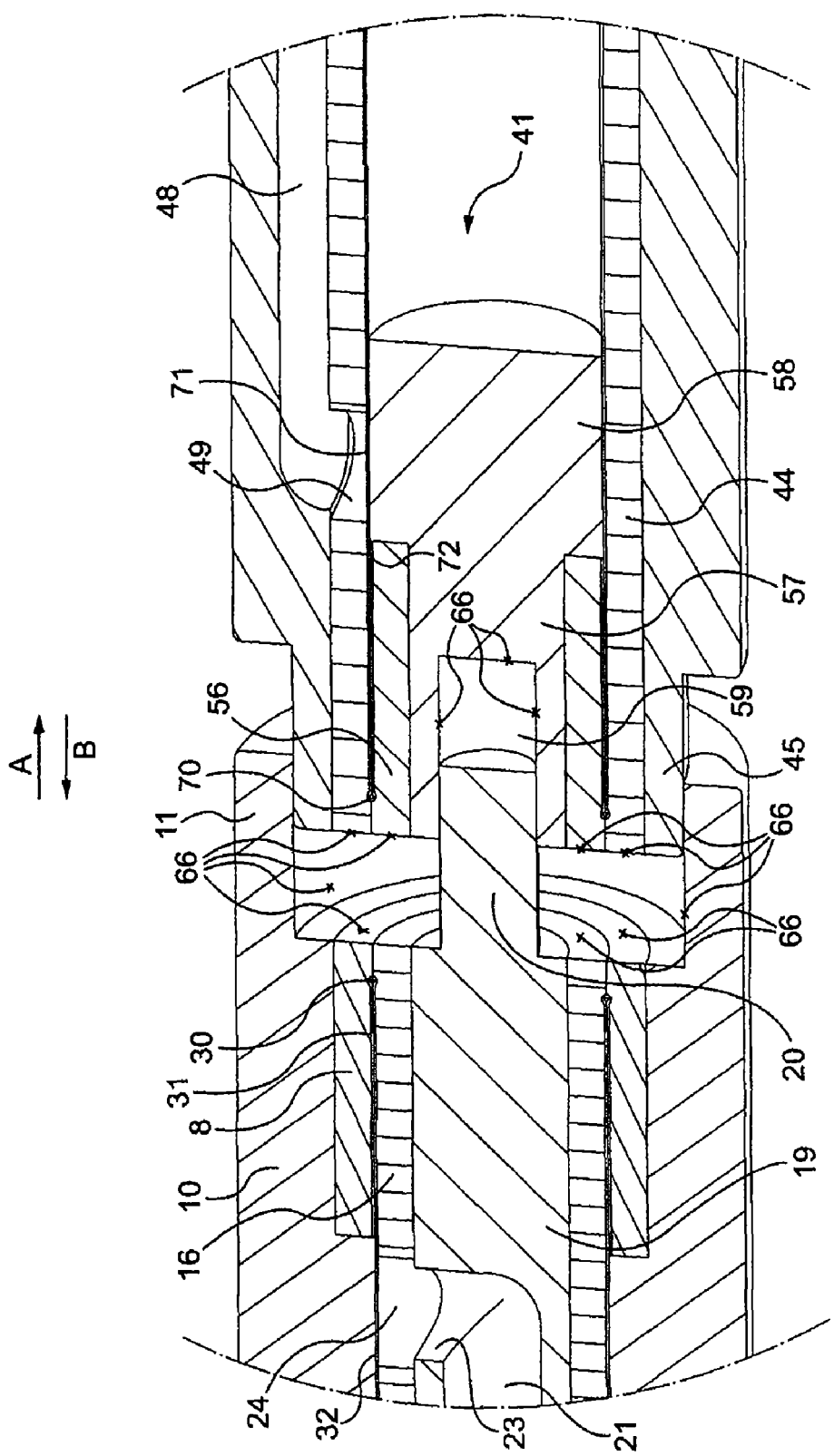

The system 1 according to the invention illustrated in FIGS. 1 to 9 comprises a male part connection device 2 and a female part connection device 3 to connect to the device 2.

The male part connection device 2 comprises a sleeve 4, a slide 5 within the sleeve 4 as well as a film 6 folded back on itself and disposed between the sleeve and the slide.

This device has a front face 12 (FIG. 3) adapted to cooperate, as will be seen below, with a front face of the female part device.

The sleeve 4 comprises a first tubular portion 7 and a second tubular portion 8 engaged within the portion 7.

Portion 7 has a cavity open at both ends and delimited by a first tubular section 9, a second tubular section 10 of greater inner diameter than that of section 9 and a third tubular section 11 of greater inner diameter that that of section 10.

The tubular portion 8 is of the same length as the section 10, of outer diameter substantially equal to the inner diameter of that section 10 and of inner diameter substantially equal to the inner diameter of the section 9.

This portion 8 is engaged in portion 7 in abutment with the shoulder situated at the junction of sections 9 and 10 with the outer face of this portion being in contact with the inner face of section 10.

Portion 8 is manufactured from an adherent rubber such as silicone whereas portion 7 is of polysulfone, these materials being resistant to temperature such that this device may be sterilized with heat, in an autoclave for example.

The slide 5 has a first cylindrical portion 15 and a second tubular portion 16 engaged around portion 15.

Portion 15 has an end piece 17, a first cylindrical section 18, a second cylindrical section 19 of smaller outer diameter than that of the section 18 and a third cylindrical section 20 of smaller outer diameter than that of section 19 and also an annular collar 25 in the neighborhood of the end of the section 18 connected to the end piece 17.

In this slide there is formed a duct 21 for liquids formed in the end piece 17 and in the sections 18 and 19 between an inlet opening 22 situated on the end piece 17 and an outlet opening 23 situated on an outer lateral face of the section 19.

The tubular portion 16 is of the same length as section 19, of outer diameter substantially equal to the inner diameters of section 9 and of portion 8 and to the outer diameter of section 18, and of inner diameter substantially equal to the outer diameter of section 19.

This portion 16 is engaged around portion 15 in abutment with the shoulder situated at the junction of sections 18 and 19 with the inner face of this portion being in contact with the outer face of section 19.

Together with section 18, this portion 16 delimits an outer lateral surface 26 of the slide (FIGS. 1 to 3).

In this portion 16 there is formed an opening 24 situated approximately half way between the edges of this portion and of the same diameter and at the same level as the opening 23.

Portion 16 is manufactured from the same adherent rubber as portion 8.

The film 6 is of polyurethane and has a thickness of $7/100^{th}$ mm. It is folded back on itself such that it has a fold 30 (FIG. 9) and, on respective opposite sides of that fold, an outer portion 31 and an inner portion 32 pressed against each other between the tubular portions 8 and 16. The opposite face of portion 31 to portion 32 is in contact with the inner face of the tubular portion 8 whereas the opposite face of portion 32 to portion 31 is in contact with the outer face of the tubular portion 16.

In the position illustrated in FIG. 1 (starting position), the outer portion 31 extends from the fold 30 of the film as far as the edge of the tubular portion 8 situated on the opposite side to face 12 whereas the inner portion 32 extends from the fold 30 of the film as far as the edge of the tubular portion 16 situated on the opposite side to face 12.

This device 2 is termed male part device since is has a moveable part (the slide in the sleeve) which, as will be seen below, is adapted to pass from a starting position to a final position in which the slide is advanced in the sleeve relative to its starting position.

The female part connection device 3 comprises a sleeve 40, a slide 41 within the sleeve 40 as well as a film 42 folded back on itself and disposed between the sleeve and the slide.

This device has a front face 60 (FIG. 3) adapted to cooperate, as will be seen below, with the front face 12 of the male part device.

The sleeve 40 comprises a first tubular portion 43 and a second tubular portion 44 engaged within the portion 43.

Portion 43 has a cavity that is open at both ends and is delimited by a first tubular section 45, a second tubular section 46 of the same inner diameter and of outer diameter greater than that of section 45 and by an end piece 47 that connects to section 46 on the opposite side to section 45.

The tubular portion 44 is of outer diameter substantially equal to the inner diameter of sections 45 and 46 and has an inner lateral face 27 (FIGS. 1 to 3) that is practically entirely covered by the tubular film 42 (FIG. 1).

This portion 44 is engaged in those sections 45 and 46, in abutment with a shoulder 63 of section 46 with the outer face of this portion being in contact with the inner face of sections 45 and 46.

Section 46 has a recessed zone delimiting, together with portion 44, a duct 48 extending from an inlet opening 49 formed in portion 44 to an outlet opening 50 at the end of the connection end piece 47.

Portion 44 is manufactured from the same rubber as portions 8 and 16.

The slide 41 has a first tubular portion 55 and a second tubular portion 56 engaged around portion 55.

Portion 55 has a first cylindrical section 57 in which a cavity 59 is formed and a second solid cylindrical section 58 of outer diameter greater than that of section 57 and substantially equal to the inner diameter of portion 44.

The tubular portion 56 is of the same length as the section 57, of outer diameter substantially equal to the outer diameter of section 58 and of inner diameter substantially equal to the outer diameter of section 57.

This portion 56 is engaged around portion 57 in abutment with the shoulder situated at the junction of sections 57 and 58 with the inner face of this portion being in contact with the outer face of section 57.

Portion 56 is manufactured from the same adherent rubber as portions 8, 16 and 44.

Like the film 6, the film 42 is of polyurethane and is of thickness $7/100^{th}$ mm. If is folded back on itself such that it has a fold 70 (FIG. 9) and, on respective opposite sides of that fold, an outer portion 71 and an inner portion 72 pressed against each other between the tubular portions 44 and 56. The opposite face of portion 71 to portion 72 is in contact with the inner face of the tubular portion 44 whereas the opposite face of portion 72 to portion 71 is in contact with the outer face of the tubular portion 56.

In the position illustrated in FIG. 1 (starting position), the outer portion 71 extends from the fold 70 of the film as far as the edge of the tubular portion 44 situated on the opposite side to face 60 whereas the inner portion 72 extends from the fold 70 of the film as far as the edge of the tubular portion 56 situated on the opposite side to face 60.

This device 3 is termed female part device since is has a moveable part (the slide in the sleeve) which, as set out below, is adapted to pass from a starting position to a final position in which the sleeve is set back in the slide relative to its starting position.

The very small thickness of the films 6 and 42 enables the pressure stresses exerted against that film to be minimized so as not to exceed the rupture limits of the material.

In the starting position of the device 2 corresponding to the position in which it is delivered (FIG. 1), section 19 is fully disposed within section 10, section 20 within section 11, the junction between the sections 19 and 20 being situated at the same level as the junction of the sections 10 and 11 with the edges of the portions of silicone 8 and 16 also being at that level, the edge surfaces of these members also being turned outwardly so forming the front face 12.

On the other side, the end piece 17 and practically the whole of section 21 project from the sleeve.

In this starting position, the film 6 is disposed such that the fold 30 is slightly withdrawn from the edges of tubes 8 and 16 situated adjacent the junction of the sections 10 and 11, and 19 and 20, the compression of the tubes 8 and 16 against each other thus providing fluid-tight protection of the film 6 adjacent their edge. The film 6 is of course itself compressed between these tubes.

In this position the openings 23 and 24 of portion 16 and of section 19 are covered by the inner portion 32 of film 6 which thus provides, by compression against portion 16, fluid-tight isolation for duct 21. A pipe not illustrated in the drawings and connected to a closed sterile device is engaged in end piece 17.

It is to be noted that in FIGS. 3 to 9 the shape of the fold 30 has been exaggerated to make it markedly more visible, the fold in reality being compressed between the portions 8 and 16, such that it has a more squashed drop-shape than that illustrated in those drawings.

The same applies for the film 42.

In the starting position of the device 3 (FIG. 1), the slide 41 is fully disposed within the sleeve 40 with the edge surfaces turned towards the exterior of sections 45, of portion 44, of portion 56 and of section 57 which are all situated at the same level to form the front face 60.

In this position the film 42 is disposed such that the fold 70 is slightly withdrawn from the free edges of the tubes 44 and 56, the compression of the tubes 44 and 56 against each other thereby providing, adjacent the face 60, fluid-tight protection for the film 42.

In this position the opening 49 of portion 44 is covered by the outer portion 71 of film 42 which thereby provides, by compression against portion 44, fluid-tight isolation to the duct 48. A pipe not illustrated in the drawings and connected to a closed sterile device is also engaged in end piece 47.

Peelable films 13 and 61 (FIG. 1) are also sealed adjacent the edges of sections 11 and 45 in order to obturate faces 12 and 60, so as to limit the number of contaminants, even though those contaminants are isolated from the surfaces to protect subsequently by virtue of the device according to the invention, by protecting the zones on which they are liable to become deposited (while the devices are not used). Plugs may also be used as a variant.

Each device 2 and 3 is sterilized beforehand and packaged for delivery. The devices 2 and 3 may be sterilized using different methods without this preventing them from being connected later.

A description will now be given, with the aid of FIGS. 1 to 8, of how to connect devices 2 and 3 together.

Figure 5:
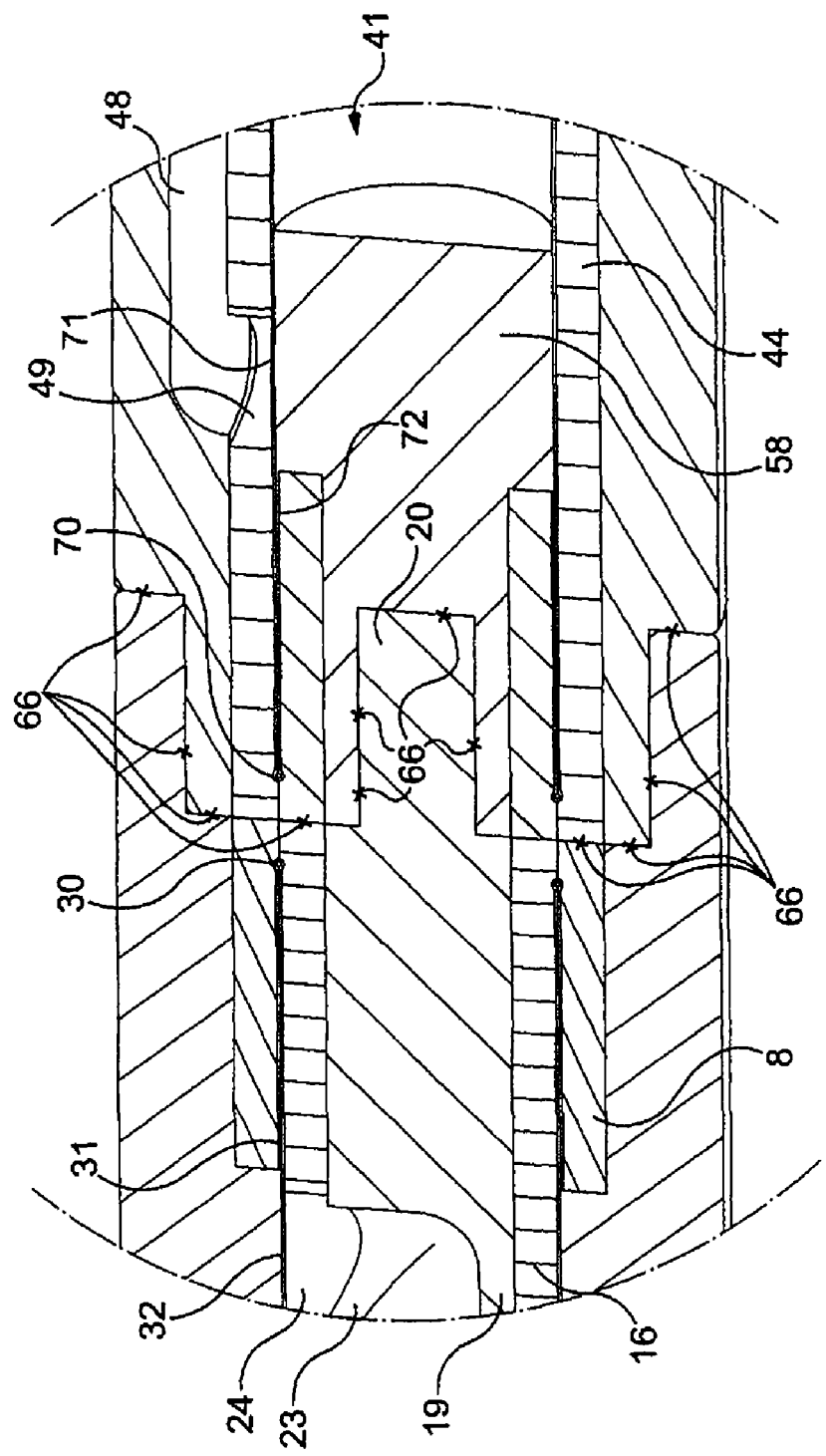
Figure 6:
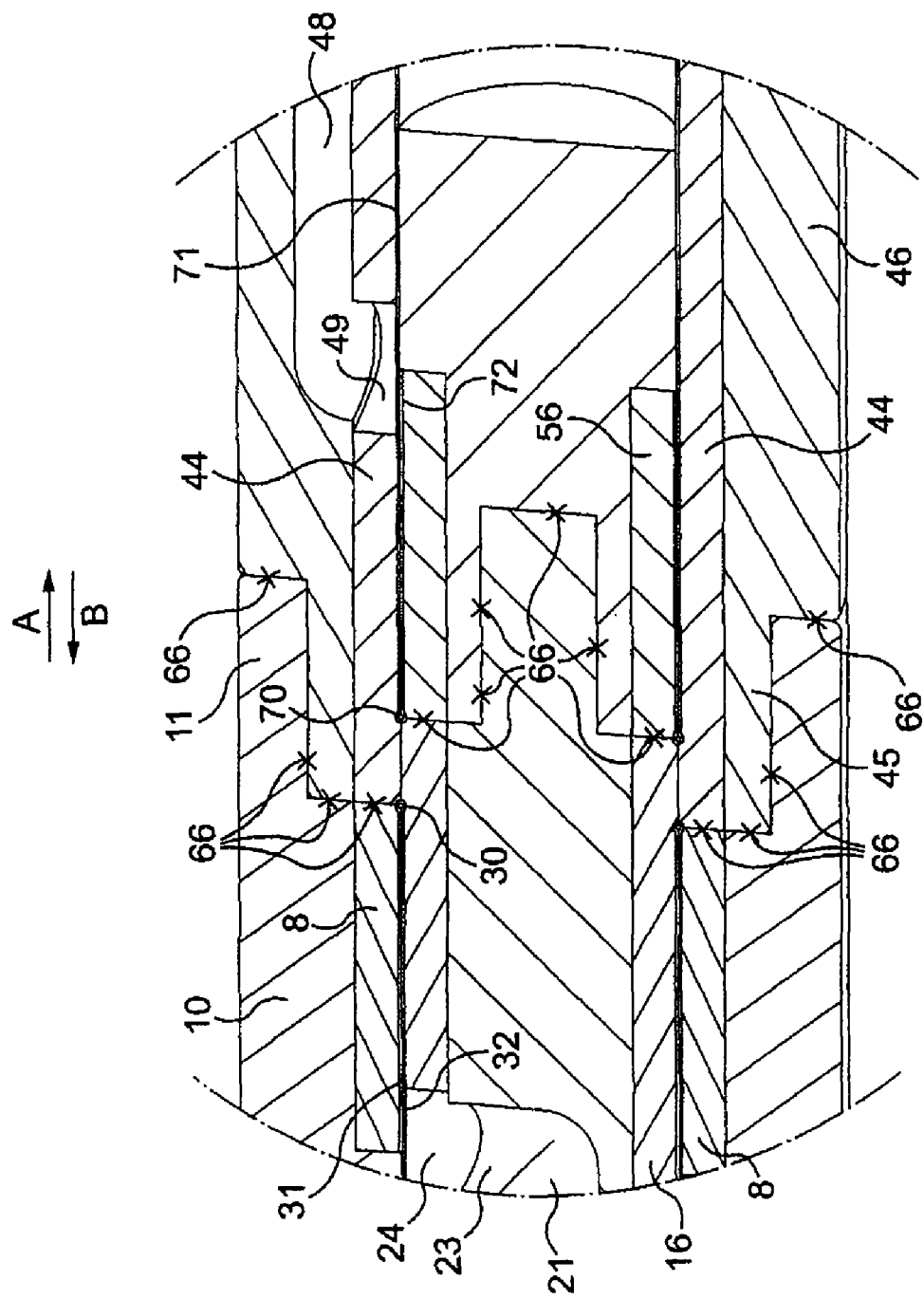

In a first phase, the operator peels the films 13 and 61 then places the device 2 in register with device 3 with the front faces 12 and 60 of the devices facing each other until contact is made as illustrated in FIG. 5, section 20 then being fully engaged in cavity 59 of section 57.

The operator then performs a sliding movement either by pulling on the sleeves in the direction of arrow B or by pushing the slides in the direction of arrow A (FIG. 6) to give rise to a relative movement of those slides relative to their respective sleeves. In the example illustrated, it is assumed that the operator acts on the slides (in the direction of arrow A) to perform the connection.

Slide 5 thus progressively enters sleeve 40 while pushing slide 41 towards the back of that sleeve.

During the movement of the slide 5, the silicone of the tubular portion 8 and of the tubular portion 16 respectively in contact with the portions 31 and 32 of the polyurethane film 6 generate sufficient friction forces with those portions 31, 32 to prevent the film 6 from sliding along those portions 8 and 16 such that the portion 32 of the film is driven to move at the same time as the slide 5 without that portion sliding along portion 16 of that slide while the portion 31 is held without sliding along the portion 8 of the sleeve.

By the same principle, if the operator acts on the sleeves rather than on the slides, it is portion 31 of the film which is driven to move at the same time as the sleeve 4 without that portion 31 sliding along the portion 8 of that sleeve while the portion 32 is held without sliding along the portion 16 of the slide 5.

The film 6 is of a material enabling the faces of the portions 31 and 32 that are in contact with each other to slide over each other.

Polyurethane is thus particularly well-adapted as it makes it possible to provide, in conjunction with the silicone of the portions 8 and 16, a non-sliding contact of the film 6 with the portions 8 and 16 while making it possible to provide a sliding contact of the portions 31 and 32 against each other.

Thus during the movement of the slide in the sleeve (or of the sleeve relative to the slide), the film 6 rolls out towards the exterior with the length of the outer portion 31 increasing and that of the inner portion 32 reducing, a part of the inner portion 32 close to the fold 30 progressing in the direction of the fold, then detaching from the portion 8 to form the fold 30 and then pressing against the portion 16 to form a part of the outer portion 31.

The fold 30 situated at the end of these portions thus moves along portion 8 (FIGS. 5 and 6) then along portion 44 (FIG. 7) in the direction of arrow A.

As the speed of movement of the fold 30 is half that of movement of portion 16 relative to portion 8, the openings 23 and 24 (FIGS. 3 to 8) approach the fold 30 progressively then pass below to reach the final position of the slide 5 (FIG. 8), advanced in the sleeve 4.

Figure 8:
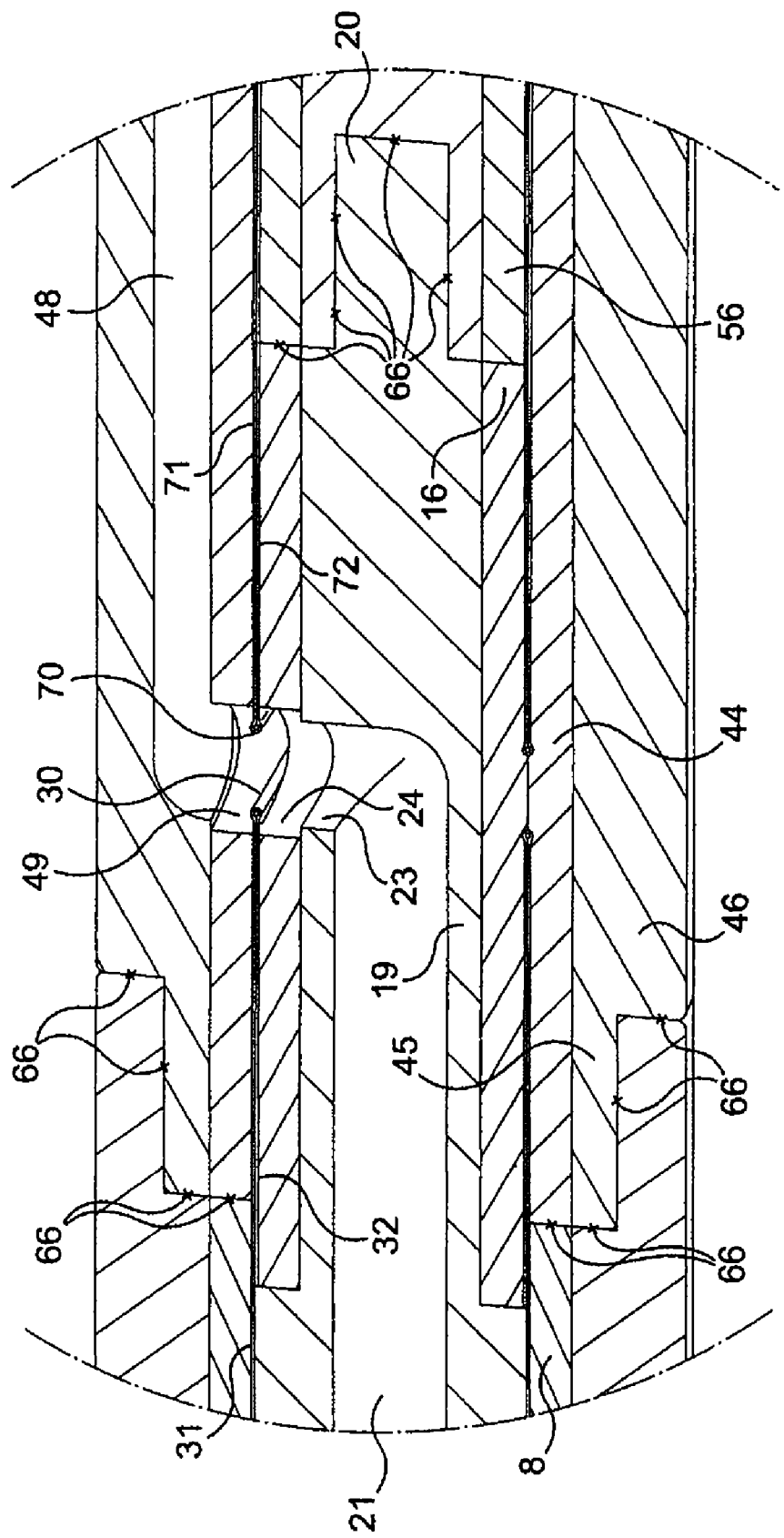
Figure 9:
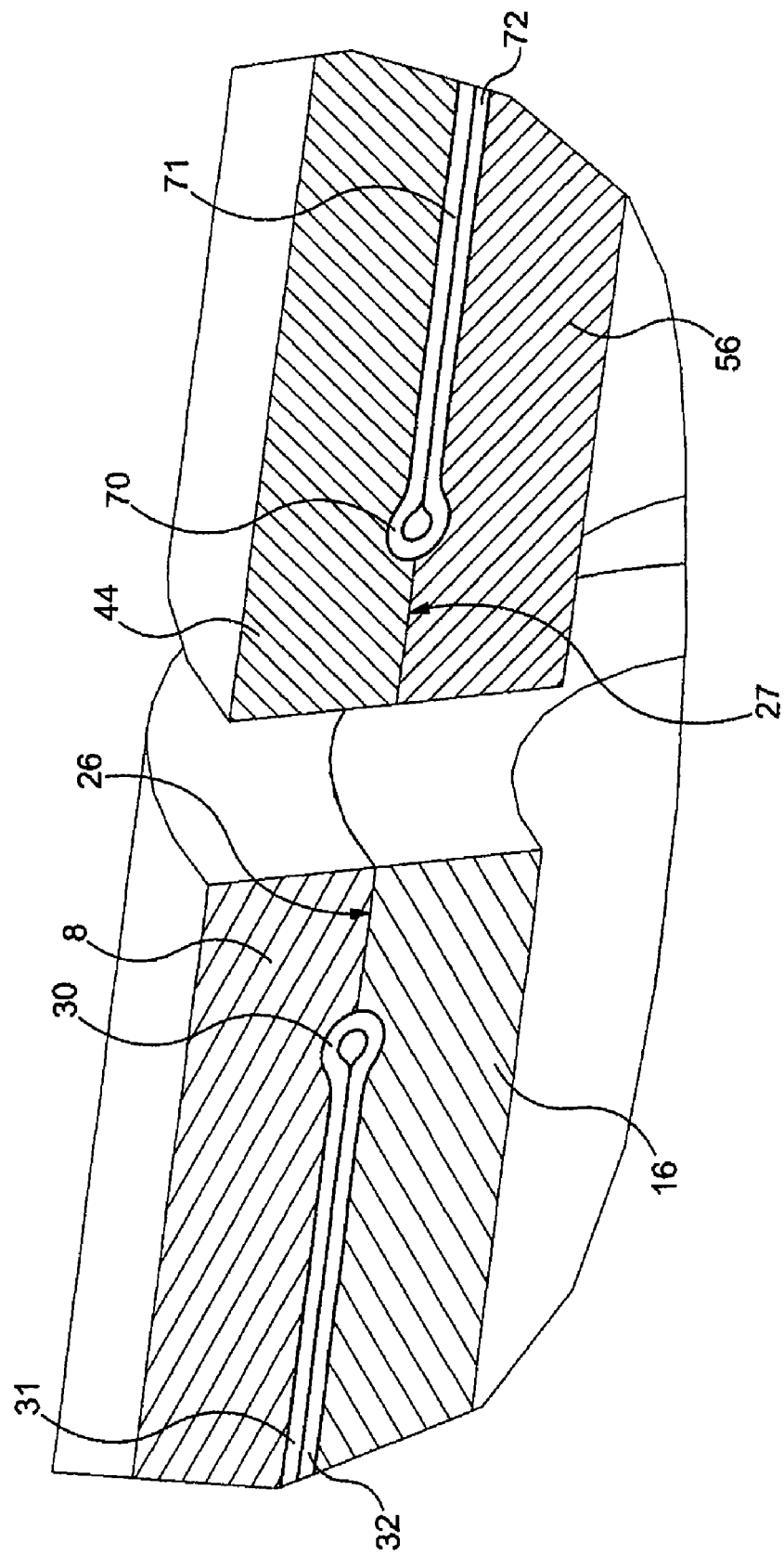
FIG. 9 is a view enlarged still further of some members of the male and female devices represented in the position which they occupy in FIG. 4.

In this final position, the collar 25 abuts the section 9 with the slide 4 projecting from the sleeve 5, sections 19 and 20 and the portion 16 being practically fully within sleeve 40, the openings 23 and 24 then being uncovered, with the fold 30 of the film being situated at the edge of those openings (FIG. 8).

Similarly, during the movement of the slide 41, the silicone of the tubular portion 44 and of the tubular portion 56 respectively in contact with the portions 71 and 72 of the polyurethane film 42 generate sufficient friction forces with those portions to prevent the film 42 from sliding along those portions 44 and 56 such that the portion 72 of the film is driven to move at the same time as the slide 41 without that portion sliding along portion 56 of that slide while the portion 71 is held without sliding along the portion 44 of the sleeve 40.

By the same principle, if the operator acts on the sleeves rather than on the slides, it is portion 71 of the film which is driven to move at the same time as the sleeve 40 without that portion 71 sliding along the portion 44 of that sleeve 40 while the portion 72 is held without sliding along the portion 56 of the slide 41.

Thus during the movement of the slide in the sleeve (or of the sleeve relative to the slide), the film 42 rolls in towards the interior with the length of the outer portion 71 reducing and that of the inner portion 71 increasing, the part of the outer portion 32 close to the fold 70 progressing in the direction of the fold, then detaching from the portion 44 to form the fold 70 and then pressing against the portion 56 to form a part of the inner portion 72.

The fold 70 situated at the end of those portions thus moves along the portion 44 (FIGS. 3 to 8) in the direction of the arrow A.

As the speed of movement of the fold 70 is half that of the movement of the portions 16 and 56 relative to the portions 8 and 44, the portion 16 of the slide 5 progressively approaches the fold 30 then passes below to attain its final position.

During this sliding the fold 70 approaches the opening 49 then passes below it to attain the final position of the slide 41 in the sleeve 40, set back in that sleeve.

In this final position the section 58 of the slide 41 abuts the shoulder 64 (FIG. 1) of the section 46 of the sleeve 40 with the opening 49 being uncovered, the fold 70 then being at the edge of that opening.

In this final position (FIG. 8) of the slides relative to their respective sleeves, the openings 23, 24 and 49 are all uncovered with those openings facing each other (the folds 30 and 70 then being at the edge of those openings) to enable the duct 21 of the slide 5 to be placed in communication with the duct 48 of the sleeve 40.

The sterile passage of liquid from the inlet opening 22 of the device 2 to the outlet opening 50 of the device 3 is thus made possible.

During these movements, the contaminants represented by crosses under the reference 66 in FIGS. 3 to 8 and liable to be present on the front surfaces 12 and 60 (for example after the films 13 and 61 have been peeled), are constantly encapsulated and isolated from the openings 24 and 49 for the whole length of the movement of the slides in the sleeves.

Figure 7:
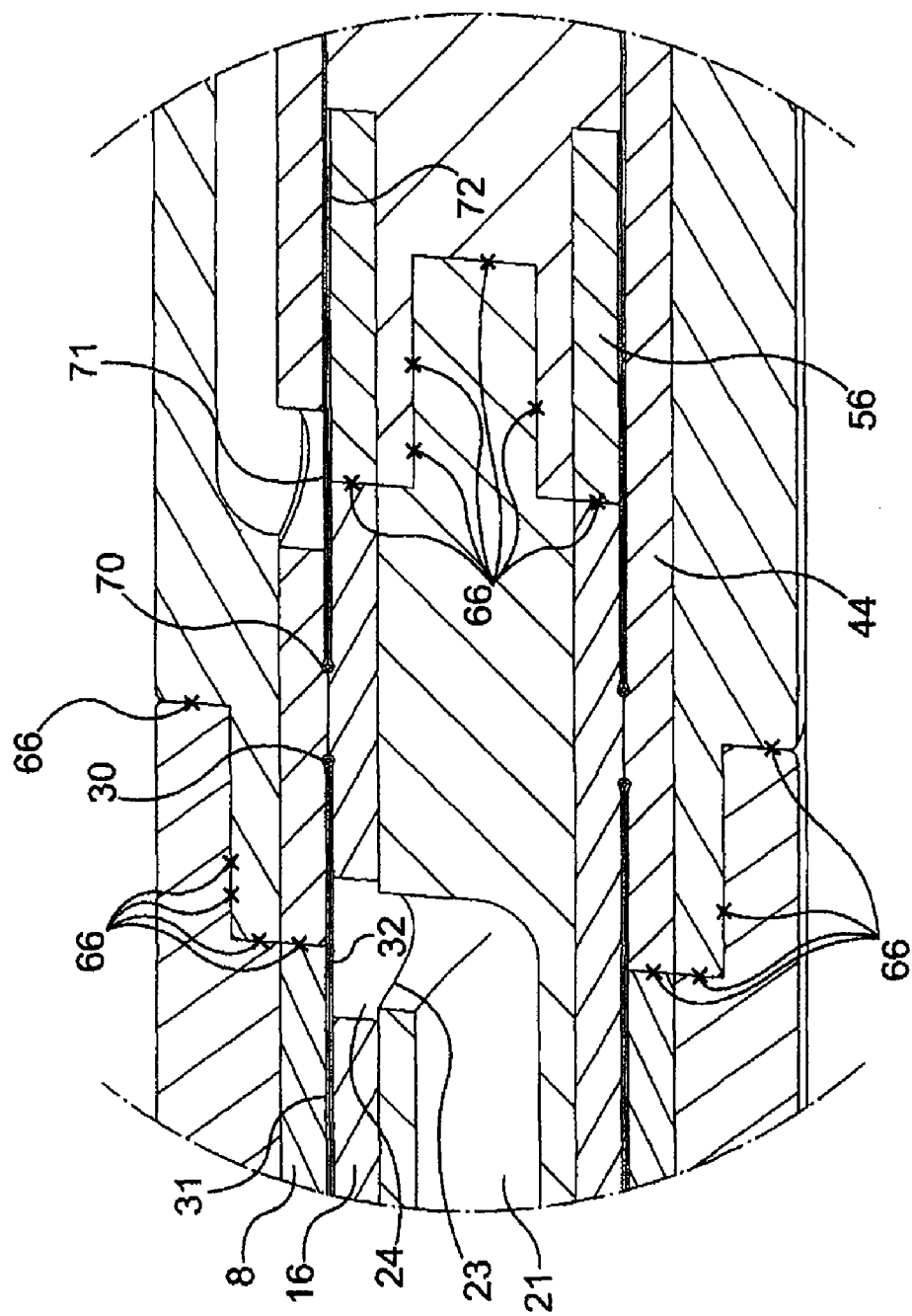

More particularly, the contaminants 66 present on the faces of the slides 5 and 41 move at the same time as the slides in the direction of arrow A until they pass under the portion 71 of the film 42 that is situated adjacent the opening 49, the film 42 thus isolating those contaminants from that opening (FIGS. 7 and 8).

In the same way, the contaminants 66 present on the faces of the sleeves 4 and 40 move in the direction of the arrow B until they pass below the outer portion 31 of the film 6 situated adjacent the openings 23 and 24, that film 6 thus isolating those contaminants from those openings (FIGS. 7 and 8).

In the advanced position of the slide 5 and set back position of the slide 41, the ducts 21 and 48 are thus placed in communication without the risk of the contaminants making those ducts unclean.

It is also possible to provide disconnection of the devices 2 and 3 by performing the reverse movement to that described above, the film 6 (respectively 42) then again arriving to cover the openings 23 and 24 (and respectively the opening 49) again to obturate them.

The films have sufficient elasticity (as well as a sufficiently small thickness) to unfold and refold repeatedly without this leading to a large and irremediable deformation of the film, the compression by the portions of silicone compensating for the possible minimal deformations of those films.

Figure 10:
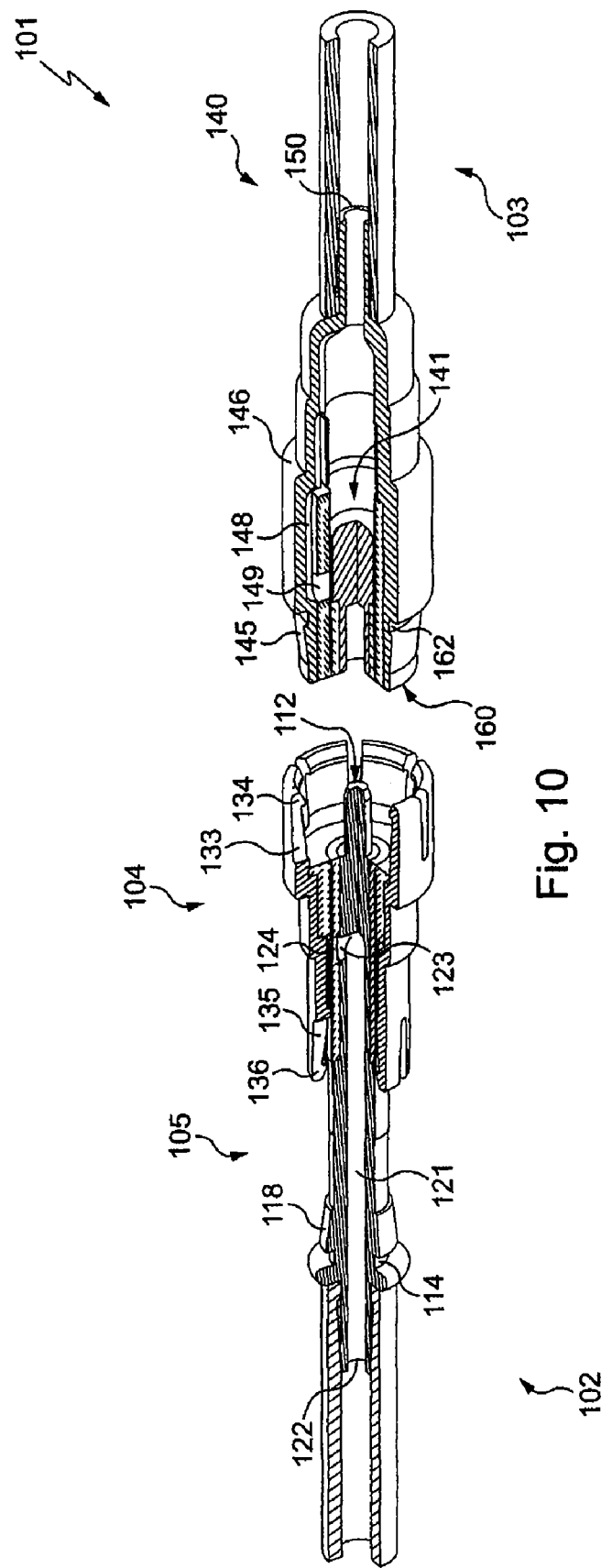
FIGS. 10 and 11 are two views similar to FIGS. 1 and 2 but for a second embodiment of the male and female connection devices according to the invention.
Figure 11:
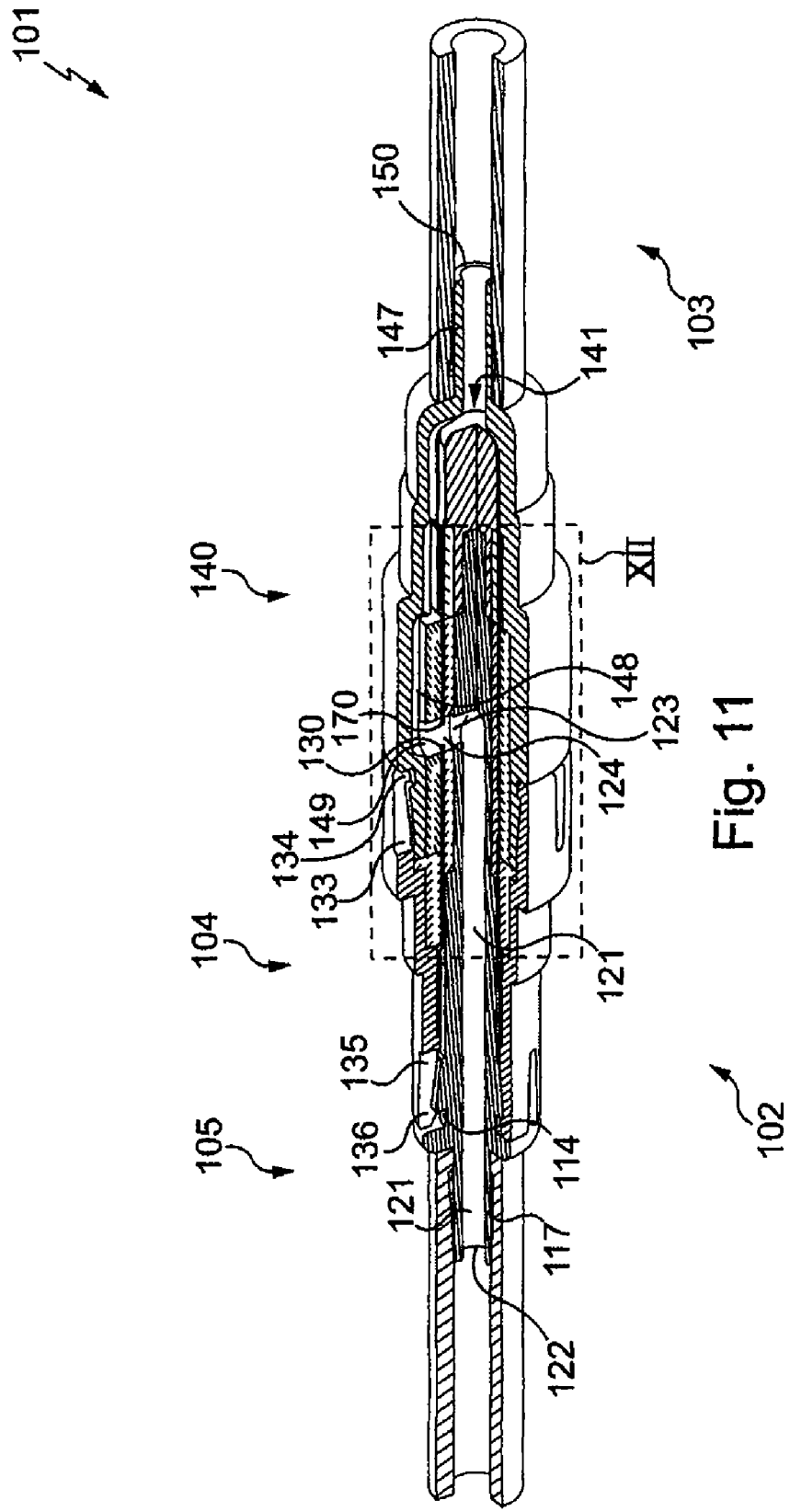
Figure 12:
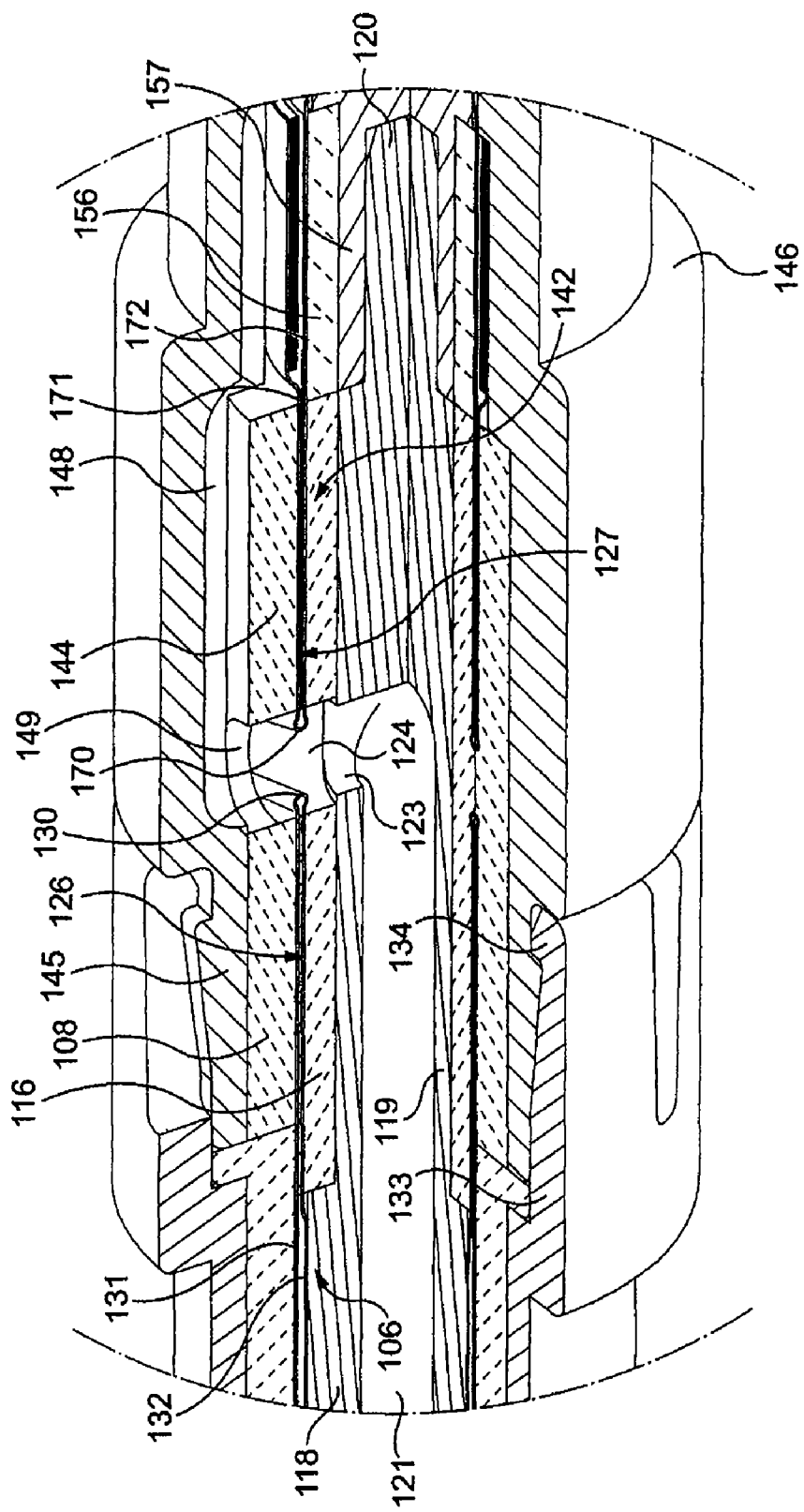
FIG. 12 is an enlarged view of the detail identified by XII in
FIG. 11.

Another embodiment of the connection devices is illustrated in FIGS. 10 to 12.

Generally speaking, the same reference numbers are used for similar elements, but increased by 100 for each embodiment.

The connection system 101 is similar to the system 1 and has a male part device 102 to connect to a female part device 103.

In this embodiment, the section 111 of the sleeve 104 of the device 102 comprises a plurality of snap-fastening feet 133 each having a tooth 134 and the section 145 of the sleeve 140 of the device 103 comprises, at the junction with the neighboring section, a groove 162 in which the teeth 134 are received by snap fastening.

The section 109 of the sleeve 104 of the device 102 comprises a plurality of snap-fastening legs 135 each having a tooth 136 and the section 118 comprises, at the junction with the end piece 117, a groove 114 in which the teeth 136 are received by snap-fastening.

In this manner, the sleeves 104 and 140 are snap-fastened one in the other with the slides being in their starting position. These slides are then moved to be brought into their final positions in which the slide of the device 102 is snap-fastened to the sleeve 104 to provide fastening in this position in which the ducts 121 and 148 are in communication by their openings 123, 124 and 149 with the folds 130 and 170 being at the edge of those openings (FIGS. 11 and 12).

Figure 13:
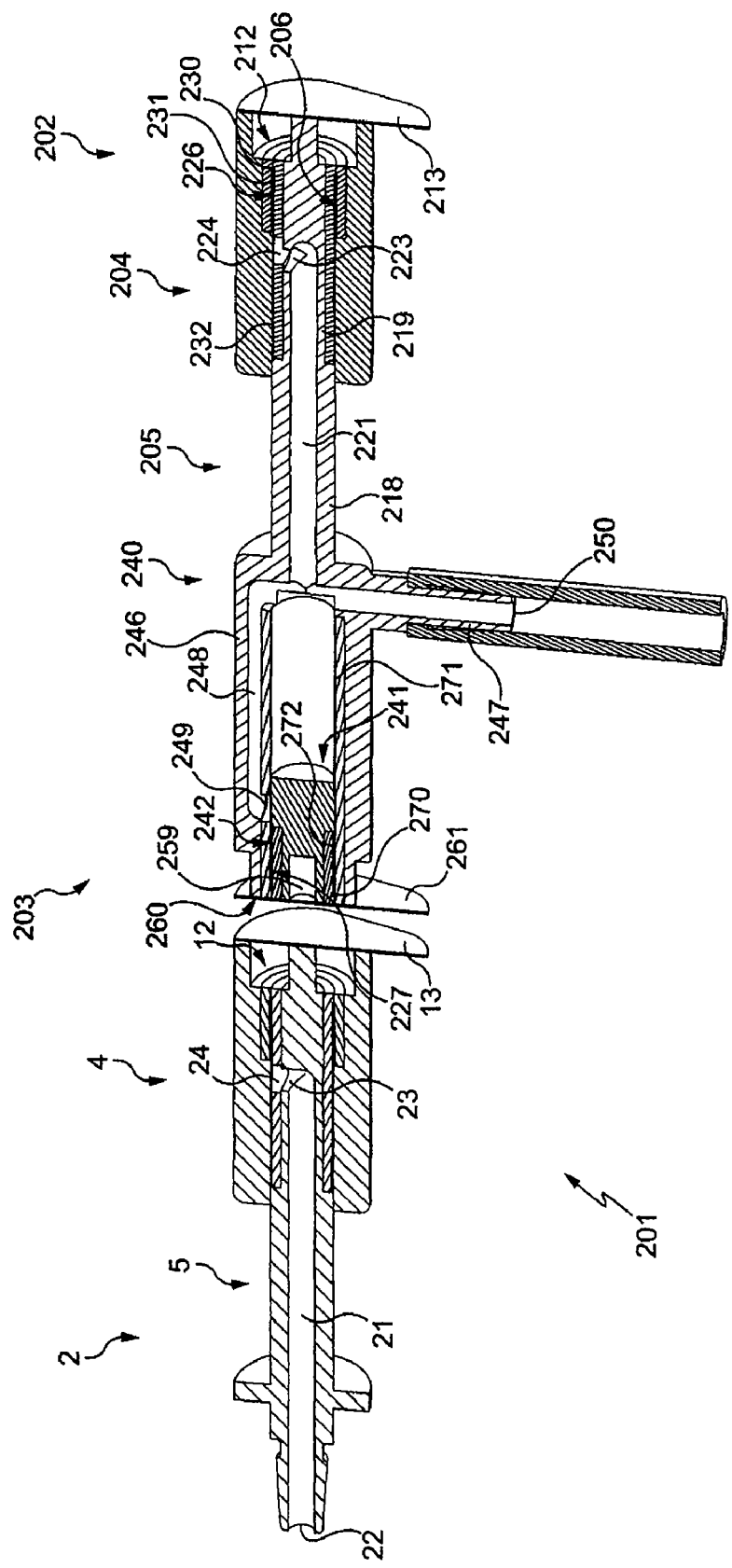
FIG. 13 is a perspective view in section of a third embodiment of the male connection device in which a female part is also present, that device being illustrated in a position in which the female part is on the point of being connected to a male connection device such as that illustrated in FIG. 1.
Figure 14:
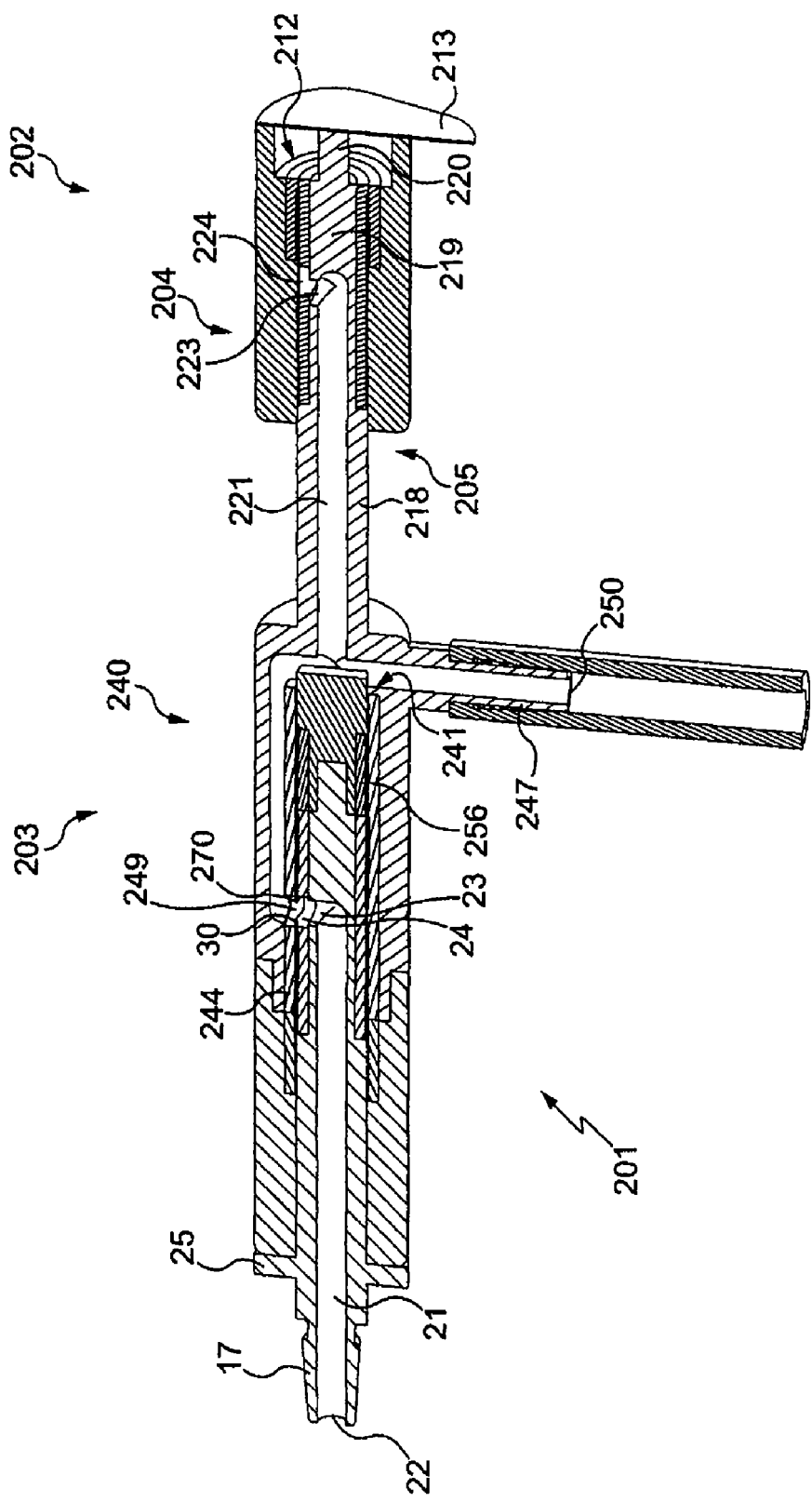
FIG. 14 is a similar view to FIG. 13 but in which the illustrated devices are engaged one within the other.

In still another embodiment illustrated in FIGS. 13 and 14, the section 246 of the female part 203 of the device has, extending in line with it, a male part 202, similar to the male part 2 and connected to the female part 203 by a tubular section 218 forming a part of the slide 205 of that male part 202.

In this embodiment the end piece 247 is situated on an outer lateral surface of the section 246 and not extending in line with it.

This device may be connected for example to devices 3 and 2 by virtue of its male part 202 and its female part 203.

It is thus for example possible, as illustrated in FIG. 13, to connect the female part 203 to a device 2 in order to make the liquid flow in the duct 248 to attain a storage pouch connected via a pipe to the end piece 247 (there is no risk of the liquid flowing through the male part 202 since, as the latter is not connected, the duct 221 is obturated in fluid-tight manner at its opening 223 by the film 206).

Once that pouch has been filled, the pipe is clamped and the device is connected by its male part 202 to a female device 3 in order to uncover the openings 223 and 224 and thereby enable the liquid to flow to a new take-off pouch.

Such devices may also be mounted in series one after the other, each male part 202 being connected to the female part 203 of the neighboring device to enable a series of take-off operations to be performed in a succession of pouches for example.

In still another embodiment not illustrated, the connection device is similar to the device having a male part 202 and female part 203 apart from the fact that it lacks the end piece 247. Such a device may for example be used to perform shunts in parallel to the main flow of a stream of liquid. This shunt may for example make it possible to client information in real time concerning the proper progress of a process or enable the liquid to flow through a new duct (if the others are obturated for example).

In still another embodiment not illustrated, this device has, between the male and female parts, a module in which a membrane is disposed to filter the liquid passing through the device.

In yet another embodiment not illustrated, the surface portion to protect is not recessed relative to the front face of the male or female device but is situated just on the edge of the front face such that the surface starts to be uncovered practically as soon as the slide moves in the sleeve to reach its final position.

In a still further embodiment not illustrated, the male or female device comprises a sensor of the physico-chemical properties of the liquid flowing through its duct.

In still another embodiment not illustrated, the male and female part connection devices are similar to the devices described earlier apart from the fact that the film of the male part device is of different diameter (greater or smaller) than that of the female part device.

In still another embodiment, the films are not of polyurethane but for example of flexible teflon (better known by the denomination "EPTFE") and/or have undergone a surface treatment to render one of their surfaces more slippery and/or the other face more adherent. In still another embodiment the outer faces of the films in the unfolded state are covered by an adhesive substance provided to strengthen the adhesion to the sleeve and to the slides while enabling the films to be detached from their corresponding sleeve and slide on passing from the starting position to the final position of the slides in the sleeves.

In other embodiments not illustrated, such devices may be formed not to obtain a sterile connection between two sets of piping intended to receive fluids but for other applications such as the connection of optical fibers or electrical contactors, for which it is necessary to maintain clean surfaces at the connection zone.

Such devices may also be implemented for placing in contact surfaces covered with chemical substances in order to produce for example a specific reaction in conditions protected from dust and/or from the air or else for placing in contact a lyophilized product in powder form situated in a first reservoir with a liquid situated in a second reservoir to reconstitute the lyophilized product. In such cases, the portions of surfaces to protect do not necessarily have openings, but may be entirely closed.

Such devices may also be used on a large scale to produce for example air locks for microbiological isolators.

The present invention is not limited to the embodiments described and represented but encompasses a variant embodiment.

The invention claimed is:

1. A connection device for a male-female connection system comprising a male part provided with a male part sleeve and with a male part slide disposed within said male part sleeve, said connection device having a male part front face, said male part slide being adapted to occupy, relative to said male part sleeve, a first starting position and a first final position in which said male part slide is advanced in said male part sleeve relative to said first starting position, said connection device also comprising a male part tubular film folded back on itself and pressed between said male part slide and said male part sleeve, said male part tubular film having, on respective opposite sides of its fold, an inner portion in at least partially non-sliding contact with said male part slide and an outer portion in at least partially non-sliding contact with said male part sleeve whereas the inner and outer portions of said male part tubular film, on movement of said male part slide in said male part sleeve from said first starting position said first final position, are adapted to slide over each other by virtue of which said fold passes, on movement of said male part slide in said male part sleeve, from a position in which a portion of outer lateral surface of said male part slide is covered by said male part tubular film to a position in which said portion of outer lateral surface is uncovered;

a female part provided with a female part sleeve and a female part slide disposed within said female part sleeve, said connection device having a female part front face, said female part slide being adapted to occupy, relative to said female part sleeve, a second starting position and a second final position in which said female part slide is set back in said female part sleeve relative to said second starting position, said connection device also comprising a female part tubular film folded back on itself and pressed between said female part slide and said female part sleeve, said female part tubular film having on respective opposite sides of its fold an inner portion in at least partially non-sliding contact with said female part slide, and an outer portion, whereas the inner and outer portions of said female part film, on movement of said female part slide in said female part sleeve from said second starting position to said second final position, are adapted to slide over each other by virtue of which said fold passes, on movement of said female part slide in said female part sleeve, from a position in which a portion of inner lateral surface of said female part sleeve is covered by said female part tubular film to a position in which said portion of inner lateral surface is uncovered.

2. The connection device according to claim 1, wherein said male part sleeve comprises a portion adapted to ensure the non-sliding contact by friction against the outer portion of said male part tubular film.

3. A The connection device according to claim 2, wherein said portion of said male part sleeve is silicone.

4. A The connection device according to claim 1, wherein said male part slide comprises a portion adapted to ensure the non-sliding contact by friction against the inner portion of said male part tubular film.

5. A The connection device according to claim 4, wherein said portion of said male part slide is silicone.

6. The connection device according to claim 1, wherein said male part tubular film is polyurethane.

7. The connection device according to claim 1, wherein in said first starting position, said fold is withdrawn from said male part front face.

8. A The connection device according to claim 1, wherein in said first starting position said male part front face of said connection device is obturated by a peelable film.

9. A The connection device according to claim 1, wherein said portion of outer lateral surface comprises an opening for access to a duct formed in said male part slide.

10. The connection device according to claim 1, wherein said female part sleeve comprises a portion adapted to ensure the non-sliding contact by friction against the outer portion of said male part tubular film.

11. The connection device according to claim 10, wherein said portion of said female part sleeve is silicone.

12. The connection device according to claim 1, wherein said female part slide comprises a portion adapted to ensure the non-sliding contact by friction against the inner portion of said female part tubular film.

13. The connection device according to claim 12, wherein said portion of said female part slide is silicone.

14. The connection device according to claim 1, wherein said female part tubular film is polyurethane.

15. The connection device according to claim 1, wherein in said second starting position, said fold is withdrawn from said female part front face.

16. The connection device according to claim 1, wherein in said second starting position said female part front face of said connection device is obturated by a peelable film.

* * * * *